(12) United States Patent
Simon et al.

(10) Patent No.: US 6,264,677 B1
(45) Date of Patent: Jul. 24, 2001

(54) WEDGE SCREW SUTURE ANCHOR

(75) Inventors: Timothy Simon, Los Alamitos, CA (US); Harold Aberman, Montclair, NJ (US)

(73) Assignee: Applied Biological Concepts, Inc., Los Alamitos, CA (US)

( * ) Notice: Subject to any disclaimer, the term of this patent is extended or adjusted under 35 U.S.C. 154(b) by 0 days.

(21) Appl. No.: 09/388,495

(22) Filed: Sep. 2, 1999

Related U.S. Application Data

(60) Continuation-in-part of application No. 09/258,049, filed on Feb. 25, 1999, now Pat. No. 5,951,560, which is a division of application No. 08/953,856, filed on Oct. 15, 1997, now Pat. No. 5,891,146.

(51) Int. Cl.$^7$ .................................................. A61B 17/04
(52) U.S. Cl. ........................... 606/232; 606/73; 411/414; 411/426
(58) Field of Search .................................. 606/60, 65, 72, 606/73, 232; 411/411, 414, 415, 424, 426

(56) References Cited

U.S. PATENT DOCUMENTS

| 5,364,400 | 11/1994 | Rego, Jr. et al. ....................... 606/72 |
| 5,456,685 | 10/1995 | Huebner ................................. 606/73 |
| 5,871,486 | 2/1999 | Huebner et al. ....................... 606/73 |

*Primary Examiner*—Michael Buiz
*Assistant Examiner*—David O. Reip
(74) *Attorney, Agent, or Firm*—Fulwider Patton Lee & Utecht, LLP

(57) ABSTRACT

A suture anchor for facilitating the anchoring of soft tissue to a bony site includes a distal sharpened tip, and intermediate threaded section and a proximal drive head. The drive head is configured to receive a socket drive tool and has a suture-receiving eyelet formed therethrough. The threaded section is defined by a crest taper angle that is greater than the root taper angle.

14 Claims, 2 Drawing Sheets

WEDGE SCREW SUTURE ANCHOR

The present application is a continuation-in-part of application Ser. No. 09/258,049, filed Feb. 25, 1999 now U.S. Pat. No. 5,951,560, which in turn is a divisional of application Ser. No. 08/953,856, filed Oct. 15, 1997, now U.S. Pat. No. 5,891,146.

FIELD OF THE INVENTION

This invention relates to wedge screws and more particularly pertains to wedge screw suture anchors for fastening soft tissue to a bony site.

BACKGROUND OF THE INVENTION

A variety of surgical procedures are known that involve the attachment of soft tissue to bone. Examples of such procedures in the shoulder include but are not limited to open and arthroscopic rotator cuff repairs of the shoulder, acromioclavicular separation repair, bankart lesion repair, biceps tenodesis, deltoid repair, and capsular shift or capsulolabral reconstruction. Representative examples of procedures in the knee include but are not limited to lateral and/or medial collateral ligament repair, iliotibial band tenodesis, patellar tendon repair and posterior tendon repair. In the elbow, ulnar or radial collateral ligament reconstruction and biceps tendon reattachment may be performed while representative foot/ankle repairs may include medial and/or lateral stabilization, Achilles tendon repair, midfoot reconstruction and hallux valgus reconstruction. Such procedures typically require the positive anchoring of a suture to the bone or bony site. The anchored suture is then attached to the muscle, tendon, ligament or other soft tissue component so as to maintain such component in position during the healing process.

Previously used suture anchors have demonstrated a tendency to pull out of the anchor site when considerable forces are applied to or generated by the soft tissue component. Additionally, it has been noted that some currently available suture anchors require an inordinate amount of torque to be applied in order to drive the anchor into the bone. Finally, some heretofore known anchor configurations do not allow the anchor to be easily retrieved in order to replace a broken suture or for replacement with a larger anchor. Thus, a need exists for a high strength suture anchor for use in surgical procedures, with which a positive anchorage is achieved and which is easily, quickly and reversibly driven into a bony site.

SUMMARY OF THE INVENTION

The present invention overcomes the shortcomings of previously known suture anchors by providing a wedge screw configuration that when properly engaged in bone will require a higher pull out force than a suture can withstand. Moreover, the anchor requires the application of a minimal amount of torque to drive into the bone. The suture anchor is driven into the bone by engaging a drive head that extends from the anchor with a socket drive tool and rotating the tool so as to thread the anchor into the bone. The anchor is easily retrievable without compromise to the surgical site by simply reversing rotation of the tool. An eyelet formed in the drive head receives a suture to which the soft tissue is subsequently attached.

The suture anchor includes a threaded section wherein a screw thread spirals about a central root structure. The root is tapered relative to the longitudinal axis of the anchor to define a root taper angle, while the crests of the threads define a crest taper angle relative to the same longitudinal axis. The device is configured such that the crest taper angle is larger than the root taper angle. Additionally, the threads are buttressed on their distal sides so as to reinforce the threads to be more capable of resisting pull-out forces. The upper threads may or may not include one or more cutting flutes to enhance the cutting action and thereby ease insertion. Any reduction in stress to the bone achieved thereby may reduce the potential for cracking.

The drive head is formed on the proximal end of the anchor while a sharpened tri-point tip is formed on its distal end to facilitate penetration into a bony mass. The larger size suture anchors may also incorporate a cutting flute in the edge of the larger diameter threads in order to minimize the risk of cracking the bone. The entire device is formed of biocompatible material.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

The figures generally illustrate a suture anchor of the present invention. The anchor is driven into bone and serves as an attachment point for a suture that is in turn affixed to soft tissue such as a muscle, tendon or ligament.

Figure 1:
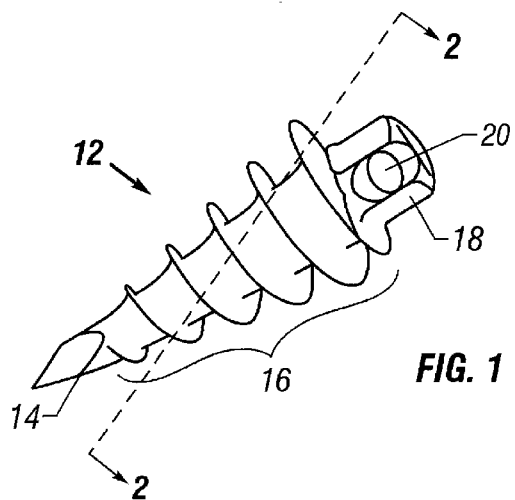
FIG. 1 is a perspective view of a suture anchor of the present invention.

FIG. 1 is a perspective view of the suture anchor 12 and clearly shows a sharp distal end 14, a threaded intermediate section 16 and at its proximal end, a raised drive head 18 having an eyelet 20 formed therethrough. The anchor is formed in various sizes to accommodate various anchoring requirements.

Figure 2:
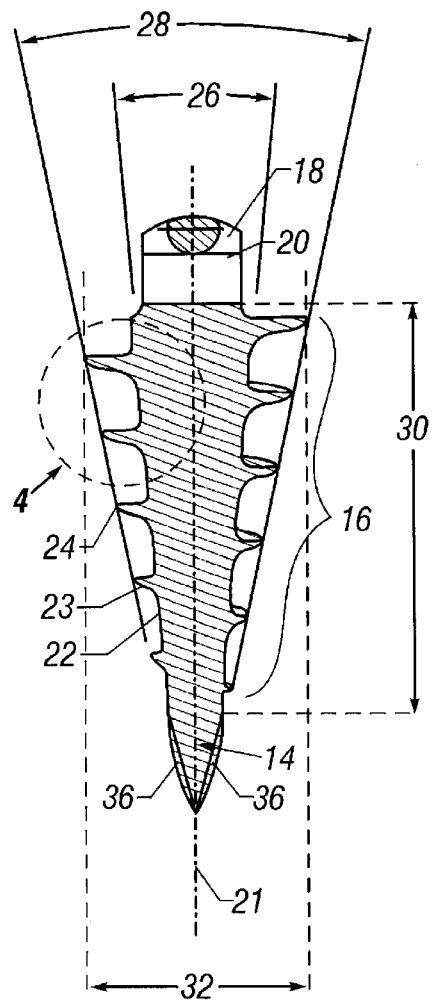
FIG. 2 is an enlarged cross-sectional view taken along lines II—II of FIG. 1.

FIG. 2 is a cross-sectional view taken along lines II—II of FIG. 1. Clearly visible in such view is the structure of the threaded section 16, which consists of a central root structure 22 having a helical thread 23 extending thereabout. The root structure is tapered with respect to the longitudinal axis 21 to define a root taper angle 26 while the thread crests 24 define a crest taper angle 26. Both the root taper angle 26 as well as the crest taper angle 28 are constant along the entire length of the threaded section 16. Of critical importance is the fact that the crest taper angle is greater than the root taper angle in all embodiments of the present invention. Depending on the overall size of the anchor, the crest taper angle may be selected in the range of from about 15° to 30° while the root taper angle is selected in the range of from about 6.0° to 15°. The thread pitch is preferably selected to be within the range of from about 0.8 to 1.5 (threads/mm).

Figure 3:
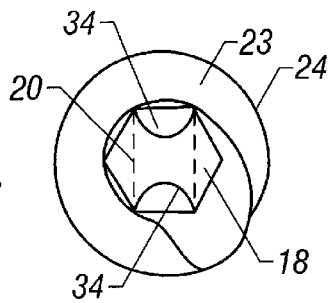
FIG. 3 is a top plan view.

FIG. 3 is a top plan view of the suture anchor 12 showing the hexagonal configuration of the drive head 18. While a hexagonal configuration is preferred, any other suitable geometries such as for example a square configuration, may alternatively be employed. Additionally clearly visible are the cupped portions 34 adjacent the ends of the eyelet 20 that allow a socket drive tool to be fitted about a drive head having a suture pre-threaded through the eyelet.

Figure 5:
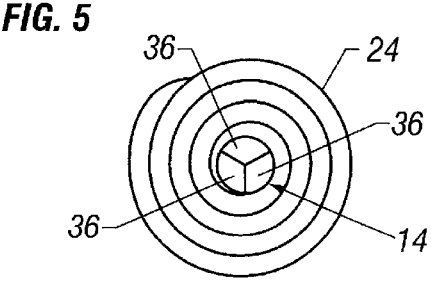
FIG. 5 is a bottom plan view.

FIG. 5 is a bottom plan view of the suture anchor 12 and clearly shows the taper of the helically configured thread crests 24. Additionally visible, are the three flat surfaces 36 of the sharpened tip 14 that form a tri-point. Such tip configuration provides for better bone cutting and penetration.

Figure 4:
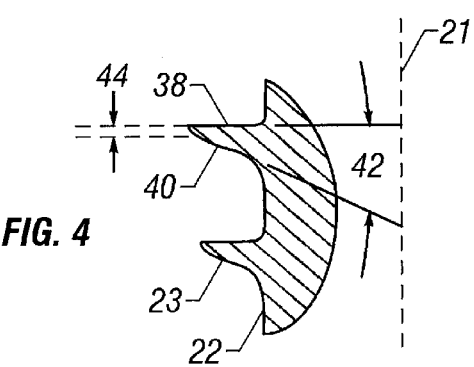
FIG. 4 is a greatly enlarged view of the circled area IV shown in FIG. 2.

FIG. 4 illustrates the buttressed nature of the threads 23 wherein the proximal surface 38 of the threads is substantially normal to the longitudinal axis 21 of the suture anchor 12 while the distal surface 40 is angled relative thereto. The angle 42 defined by the convergence of the two surfaces comprises approximately 20°. This provides additional support for the threads and helps the threads resist distortion upon being subjected to pull-out forces. The edge thickness 44 of the threads 23 is constant along the entire length of the screw thread and is selected to be in the range of from about 0.08 mm to about 0.3 mm.

The following dimensional combinations, also including the length 30 and width 32 of the threaded segment 16, are preferred:

| width(32) | length(30) | root taper angle(26) | crest taper angle(28) | pitch | edge width(44) |
|---|---|---|---|---|---|
| 1.9 mm | 4.0 mm | 7.5° | 18° | .8 | .11 mm |
| 2.7 | 5.0 | 8.0 | 21 | 1.0 | .10 |
| 3.4 | 6.0 | 12 | 22 | 1.2 | .10 |
| 4.5 | 7.5 | 10 | 24 | 1.5 | 0.08 |
| 5.0 | 8.0 | 11 | 26 | 1.5 | 0.08 |

The suture anchor is preferably formed of a biocompatible material such as titanium alloy, a non-absorbable polymer, a bioabsorbable polymer, a ceramic material or a bioceramic material any one of which can also be coated with a bioabsorbable coating having a low coefficient of friction. The coating can also include a pharmacological agent or bone growth factor. The use of bioabsorbable polymers or ceramic materials may require the tapping of a pilot hole prior to insertion.

Figure 6:
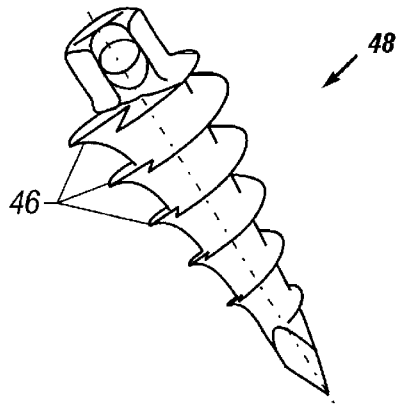
FIG. 6 is a perspective view of an alternative embodiment of the present invention.
Figure 7:
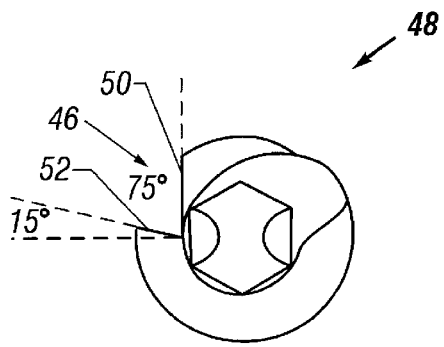
FIG. 7 is a top plan view of the suture anchor shown in FIG. 6.

FIGS. 6 and 7 illustrate an alternative embodiment wherein a single cutting flute 46 is formed in each of the top three windings of the screw thread of suture anchor 48. Each of the cutting flutes extends to the full depth of the thread to the root structure wherein the leading edge 50 that defines each cutting flute is tangent to the root structure while the trailing edge 52 is angled 75° relative thereto. The three cutting flutes are longitudinally aligned with one another.

Figure 8:
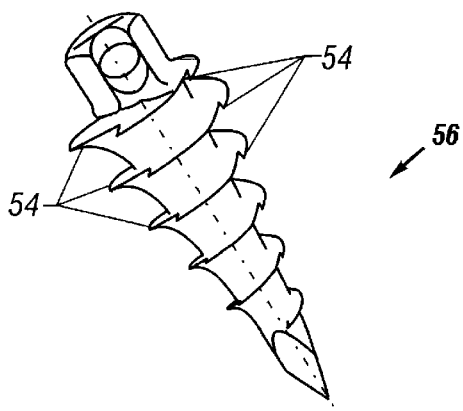
FIG. 8 is a perspective view of another alternative embodiment of the present invention.
Figure 9:
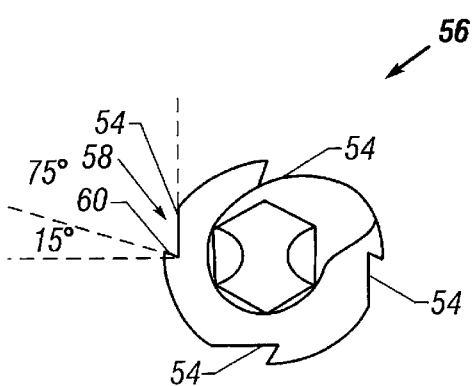
FIG. 9 is a top plan view of the suture anchor shown in FIG. 8.

FIGS. 8 and 9 illustrate a further alternative embodiment wherein four cutting flutes 54 are formed in each of the top three windings of the screw thread of the suture anchor 56. Each of the cutting flutes extend to approximately one half the thread depth wherein the leading edge 58 that defines each flute is tangent to the root structure and the trailing edge 60 is angled at 75° relative thereto. Each of the four cutting flutes are longitudinally aligned with the cutting flutes formed in the adjacent threads.

In use, a small pilot hole may optionally first be drilled into the bony site. A suture anchor 12 of the appropriate size is selected which may optionally be pre-threaded with the appropriate suture. The sharp tip 14 of the suture anchor is placed in the pilot hole and the anchor is rotated into place with a socket drive tool that engages the anchor's drive head 18. At the appropriate depth, the socket tool is disengaged from the suture anchor to leave behind the anchor and attached suture. The suture is then used to attach the soft tissue to the anchor site. In the event the suture fails or it is determined that a larger anchor is needed, the previously implanted anchor is easily removed by again fitting the socket drive tool to the drive head and rotating in a counter-clockwise direction. A plurality of such anchors may be utilized to effect a single repair.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A suture anchor for anchoring soft tissue to bone, comprising:

a threaded section including a tapered root structure about which a helical screw thread is formed wherein said tapered root structure defines a uniform root taper angle relative to a longitudinal axis and said screw thread includes a peripheral crest which defines a uniform crest taper angle relative to said axis and wherein said crest taper angle is greater than said root taper angle;

a sharpened distal end; and a proximal drive head configured to receive a socket drive tool wherein said drive head has an eyelet formed therein configured to receive a suture.

2. The suture anchor of claim 1 wherein said root taper angle is selected to be in the range of from about 6° to 15° and said crest taper angle is selected to be in the range of from about 15° to 30°.

3. The suture anchor of claim 1, wherein said helical screw thread is buttressed on its distal surface.

4. The suture anchor of claim 1, wherein said drive head has a hexagonal configuration.

5. The suture anchor of claim 1, wherein said drive head is cupped at the ends of the eyelet that is formed therethrough in order to accommodate a suture therein whereby a socket drive tool in engagement with said drive head would avoid interference with a pre-threaded suture.

6. The suture anchor of claim 1, wherein said sharpened distal end comprises a tri-point.

7. The suture anchor of claim 1 wholly formed of biocompatible material.

8. The suture anchor of claim 7, wherein said biocompatible material comprises a titanium alloy.

9. The suture anchor of claim 7, wherein said biocompatible material comprises a polymer.

10. The suture anchor of claim 9, wherein said polymer is bioabsorbable.

11. The suture anchor of claim 1, wherein said screw thread has cutting flutes formed therein.

12. The suture anchor of claim 11, wherein said cutting flutes are formed in the distal most two to three windings of said screw thread.

13. The suture anchor of claim 11, wherein said cutting flutes are limited to one cutting flute per winding of the screw thread and wherein each such cutting flute extends to said root structure.

14. The suture anchor of claim 11 wherein multiple cutting flutes are formed in a winding of said screw thread and wherein each such cutting flute extends approximately half way to said root structure.

* * * * *